(12) United States Patent
Richelsoph et al.

(10) Patent No.: US 8,221,504 B2
(45) Date of Patent: Jul. 17, 2012

(54) COATING AN IMPLANT FOR INCREASED BONE IN-GROWTH

(75) Inventors: Kelly C. Richelsoph, Memphis, TN (US); Linda Morris, Arlington, TN (US); Jantzen A. Cole, Memphis, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 1931 days.

(21) Appl. No.: 11/063,797

(22) Filed: Feb. 23, 2005

(65) Prior Publication Data

US 2006/0188541 A1    Aug. 24, 2006

(51) Int. Cl.
*A61F 2/36* (2006.01)

(52) U.S. Cl. .............. 623/23.3; 623/11.11; 623/16.11; 623/18.11; 623/22.11; 623/22.21; 623/23.15; 424/422; 424/423; 427/2.1; 427/2.24

(58) Field of Classification Search ............... 623/23.62
See application file for complete search history.

(56) References Cited

U.S. PATENT DOCUMENTS

| | | | | |
|---|---|---|---|---|
| 5,487,897 | A * | 1/1996 | Polson et al. | 424/426 |
| 5,614,206 | A | 3/1997 | Randolph et al. | |
| 5,807,567 | A | 9/1998 | Randolph et al. | |
| 6,136,029 | A | 10/2000 | Johnson et al. | |
| 6,296,667 | B1 | 10/2001 | Johnson et al. | |
| 6,790,228 | B2 | 9/2004 | Hossainy et al. | |
| 6,984,236 | B2 * | 1/2006 | Raab | 606/76 |
| 2002/0169066 | A1 | 11/2002 | Cassidy et al. | |
| 2004/0002766 | A1 * | 1/2004 | Hunter et al. | 623/20.21 |

FOREIGN PATENT DOCUMENTS

| | | |
|---|---|---|
| EP | 0071242 | 7/1982 |
| WO | WO01/12106 | 2/2001 |

OTHER PUBLICATIONS

OSTEOSET® Resorbable Mini-Bead Kit. Product brochure [online]. Wright Medical Technology, 2003 [retrieved on May 22, 2008]. Retrieved from the Internet:<URL: http://web.archive.org/web/20030205113815/www.wmt.com/Physicians/ProductDetail.asp?CatID=1&id=1021483800.*

OSTEOSET® Sale Sheet. Sales sheet [online]. Wright Medical Technology, 2008 [retrieved on May 23, 2008]. Retrieved from the Internet<URL http://www.wmt.com/Physicians/prescribing/docs/en/134341-0.pdf.*

* cited by examiner

*Primary Examiner* — Frederick Krass
*Assistant Examiner* — Nannette Holloman
(74) *Attorney, Agent, or Firm* — Duane Morris LLP (57) ABSTRACT

A method of preparing an implant for bone in-growth comprising: providing a metal implant body, the metal implant body having a metal load bearing layer on an outer surface, the metal load bearing layer having a plurality of pores therein, the pores configured to promote bone in-growth into the load bearing layer; providing calcium sulfate hemi-hydrate; providing a diluent; mixing the calcium sulfate hemi-hydrate and the diluent to form a calcium sulfate paste; applying the calcium sulfate paste to the load bearing layer such that the calcium paste substantially impregnates at least a portion of the pores and forms an excess layer of the calcium sulfate paste on an outer surface of the load bearing layer; and wiping the calcium sulfate paste to remove the excess layer and thereby expose the outer surface of the load bearing layer while leaving the calcium sulfate paste impregnated in the pores.

20 Claims, 8 Drawing Sheets

Figure 6A - Control

COATING AN IMPLANT FOR INCREASED BONE IN-GROWTH

CROSS REFERENCE TO RELATED APPLICATIONS

Not applicable

STATEMENT REGARDING FEDERALLY SPONSORED RESEARCH OR DEVELOPMENT

Not applicable

REFERENCE TO A MICROFICHE APPENDIX

Not applicable

FIELD OF THE INVENTION

The present invention relates to orthopedic implants, and more particularly to implants having an outer surface configured to promote bone in-growth.

BACKGROUND OF THE INVENTION

Calcium sulfate, also known as Plaster of Paris, is known to be an osteoconductive material, and is used in various forms to fill bone voids and increase osteogenesis. Applicant Wright Medical Technology, Inc. is a leading manufacturer of calcium sulfate-based bone repair materials (OSTEOSET® pellets; ALLOMATRIX® bone putty; MIIG® injectable bone putty). When calcium sulfate hemihydrate ($CaSO_4.1/2H_2O$) is mixed with water, it forms a paste, which soon crystallizes into a solid form, calcium sulfate di-hydrate ($CaSO_4.2H_2O$). Although the crystalline form of calcium sulfate is relatively hard, it is also brittle and lacks sufficient compaction strength to serve as a load bearing structure in prosthetic implants. Perhaps for this reason, little effort has been made to incorporate calcium sulfate into implants. Instead, calcium sulfate is typically used as an adjunct to an implant procedure, such as to fill bone voids around an implant. For example, U.S. Pat. No. 5,147,403 (Gitelis), which is incorporated herein by reference, is directed to the problem of filling gaps between an implantable prosthesis and the patient's bone. Gitelis teaches solving the problem by applying calcium sulfate in free-flowing form to the receiving surface of the host bone and then seating the prosthesis in the receiving surface, such that the calcium sulfate fills one or more of the gaps resulting between the prosthesis and the host bone. Gitellis does not teach or suggest using a porous coating on the implant, filling a porous coating with calcium sulfate, nor wiping off excess coating to preserve a load bearing surface.

Implants having a porous surface configured to promote bone in-growth are well known. Porous implants have the advantage of being implantable without the use of bone cement. Various types of porous implant surfaces have been developed. U.S. Pat. No. 3,605,123 (Hahn), which is incorporated herein by reference, discloses a dense metal base and an overlying highly porous metallic layer which permits growth of bone tissue into the pores. U.S. Pat. No. 3,855,638 (Pilliar), which is incorporated herein by reference, describes a prosthetic device comprised of a solid metallic material substrate and a porous coating of metallic material adhered to and extending over a portion of the substrate surface. The porous coating consists of a plurality of small ball-shaped metallic particles that are bonded together at their points of contact with each other and the substrate to define a plurality of connected, interstitial pores uniformly distributed throughout the coating. The porous coating is suitable for ingrowth of boney tissue into the porous coating.

U.S. Pat. No. 3,906,550 (Rostoker, et al), which is incorporated herein by reference, describes a prosthetic device which includes a porous fiber metal structure formed from substantially sinusoidally shaped fiber strands. The points of contact between the fibers are metallurgically bonded by a sintering process. This fiber metal structure provides at least a portion of the surface of the prosthetic device adjacent to the skeletal structure to enable bone and soft tissue growth into the fiber metal structure.

U.S. Pat. No. 4,715,860 (Amstutz et al.), which is incorporated herein by reference, describes an acetabular cup for an artificial hip joint that is provided with a right cylindrical portion and chamfered dome which is of porous titanium or other suitable material, including a coating of either sintered fibers or sintered small particles such as spheres, to encourage early bone ingrowth following force fit insertion of the cup into the acetabulum.

U.S. Pat. No. 4,834,756 (Kenna), which is incorporated herein by reference, describes a metallic bone prosthesis having a porous coating for bone ingrowth or interlocking with bone cement. The porous coating comprises two layers of generally ball-shaped metallic particles bonded together at their points of contact, e.g. by sintering, and defining between them a plurality of connected interstitial pores having an average pore size of from about 350 microns to about 500 microns.

U.S. Pat. Nos. 6,136,229 (Johnson) and 6,296,667 (Johnson), which are incorporated herein by reference, make the following observations concerning metals that can be used to form porous frameworks:

> Metals which can be used to form the hard, strong, continuous framework component include titanium, stainless steels, cobalt/chrome alloys, tantalum, titanium-nickel alloys such as Nitinol and other superelastic metal alloys. Reference is made to Itin, et al., "Mechanical Properties and Shape Memory of Porous Nitinol," Materials Characterization [32] pp. 179-187(1994); Bobyn, et al., "Bone Ingrowth Kinetics and Interface Mechanics of a Porous Tantalum Implant Material," Transactions of the 43rd Annual Meeting, Orthopaedic Research Society, p. 758, Feb. 9-13, 1997 San Francisco, Calif.; and to Pederson, et al., "Finite Element Characterization of a Porous Tantalum Material for Treatment of A vascular Necrosis," Transactions of the 43rd Annual Meeting, Orthopaedic Research Society, p. 598 Feb. 9-13, 1997. San Francisco, Calif., the teachings of all of which are incorporated by reference. Metals can be formed into hard, strong, continuous supportive frameworks by a variety of manufacturing procedures including combustion synthesis, plating onto a "foam" substrate, chemical vapor deposition (see U.S. Pat. No. 5,282,861), lost mold techniques (see U.S. Pat. No. 3,616,841), foaming molten metal (see U.S. Pat. Nos. 5,281,251, 3,816,952 and 3,790,365) and replication of reticulated polymeric foams with a slurry of metal powder as described for ceramic powders.

Incorporation of osteoconductive and osteoinductive materials into the surface of implants is known. However, most prior art uses of osteoconductive implant coatings focus on calcium phosphate, which can form hard crystalline structures such as hydroxyapatite. For example, U.S. Pat. Nos. 6,136,229 (Johnson) and 6,296,667 (Johnson) note:

> By and large, metal or ceramic materials that have been proposed for bone substitutes have been of low porosity and have involved substantially dense metals and ceramics with semi-porous surfaces filled or coated with a calcium phosphate based material. The resulting structure has a dense metal or ceramic core and a surface which is a composite of the core material and a calcium phosphate, or a surface which is essentially a calcium phosphate. The bone substitute materials of this type commonly are heavy and dense, and often are significantly stiffer in structure than bone. Reference here is made to U.S. Pat. No. 5,306,673 (Hermansson et al.), U.S. Pat. No. 4,599,085 (Riess et al.), U.S. Pat. No. 4,626,392 (Kondo et al.), and U.S. Pat. No. 4,967,509 (Tamari et al.).

Prior art methods of providing implants with osteogenic calcium phosphate materials have generally been complex, and therefore expensive. For example U.S. Pat. No. 5,306,673 (Hermansson) discloses a method of manufacturing a composite ceramic material having a high strength combined with bioactive properties when the material is used as a dental or orthopedic implant. The method includes preparing a powder mixture, mainly comprising partly a first powder, which in its used chemical state will constitute a bioinert matrix in the finished material, and partly a second powder, mainly comprising a calcium phosphate-based material. The first powder comprises at least one of the oxides belonging to the group consisting of titanium dioxide ($TiO_2$), zirconium oxide ($ZrO_2$) and aluminum oxide ($Al_2O_3$). The second powder mainly comprises at least one of the compounds hydroxylapatite and tricalcium phosphate. A raw compact is made of the powder mixture. The raw compact is densified through an isostatic pressing in a hot condition (HIP) at a pressure higher than 50 MPa to produce a composite material. The resulting composite material is a matrix that comprises one or several metal oxides of the first powder, and in which hydroxylapatite and/or tricalcium phosphate is evenly dispersed. The invention also relates to a composite ceramic material as well as a body, completely or partially made of this material.

Another example of complexity is provided by U.S. Pat. No. 4,599,085 (Riess et al.), which discloses a bone implant member which is characterized in that the support or carrier material is a biocompatible metal, such as titanium, tantalum, niobium or a similar harmless sintered metal which is capable of bonding with calcium phosphate ceramic without the formation of intermediate reaction products. Reiss discloses that calcium phosphate ceramics which are present as a powder in a finely-dispersed up to lumpy form can be combined with titanium powder of a somewhat similar grain size into a compound material through a pressing or sintering process, which evidences the physical and chemical advantages of the sum of the individual materials. The sintering temperature lies within a range of over 1500° K. (degrees Kelvin) up to 2300° K. in conformance with the intended sintering density of the calcium phosphate support member. The implant member includes, at least at the sides facing towards the bone surface in the implant space within the bone, a surface layer consisting completely of calcium phosphate, particularly tricalcium phosphate. Due to obtained experimental and clinical experiences, the pure calcium phosphate surface layer should have the thickness of about 0.1 to 0.5 mm. the surface layer of pure calcium phosphate is pressed on the implant member through the intermediary of a further pressure-sintering process. The sintered tricalcium phosphate surface layer is homogeneously interconnected with the calcium phosphate particles containing metal-calcium phosphate in the compound material whereas, in the compound material itself, there is present more than one mechanical bond between metal and calcium phosphate, so that the tricalcium phosphate surface layer is present in a fixed bonded formation with the support member.

U.S. Pat. No. 5,108,436 (Chu et al.) discloses methods for incorporating a osteogenic proteins into stress-bearing members: "A number of procedures may be used to combine the stress-bearing member with an osteoinductive composition. The simplest procedure is to coat or dip the stress-bearing member with a solution of OFE, or a suspension containing the osteogenic protein and TGF-beta. Sufficient OFE or suspension of the osteogenic protein and TGF-beta is applied to completely cover the portion of the stress-bearing member to be fixed by bone ingrowth. Alternatively, sufficient amounts of the osteoinductive composition may be applied to completely saturate the stress-bearing member." (Col. 6, lines 9-19). Chu further states: "The solution of OFE or suspension containing the osteoinductive protein and TGF-beta may be further air-dried or freeze-dried onto the stress-bearing member to provide a dry osteoinductive prosthesis." (Col. 6, lines 47-51). Chu discloses that the osteogenic protein is will normally be formulated in osteogenically effective amounts with pharmaceutically acceptable solid or fluid carriers. Preferably, the formulations include a matrix that is capable of providing a structure for developing bone and cartilage. Potential matrices may be biodegradable or nonbiodegradable, and may be chemically or biologically defined. Although the Chu invention appears to have been directed toward a collagen carrier, it also mentions the use of calcium sulfate: "Other preferred pharmaceutically acceptable carriers may be materials such as calcium sulfate, hydroxyapatite, tricalcium phosphate, polyorthoesters, polylactic-polyglycolic acid copolymers, bioglass, and the like." (Col. 6, lines 3-6).

In contrast with calcium phosphate, little effort has been made to incorporate calcium sulfate into implants. Applicant is aware of three examples in U.S. Pat. No. 6,136,029 (Johnson), U.S. Pat. No. 6,296,667 (Johnson) and U.S. P.A.P. 2002/0169066 (Cassidy et al.), all of which are incorporated herein by reference (and all of which are owned by applicant, Wright Medical). Each of these patent documents discloses the general concept of providing a porous structure having an osteoconductive component, as well as providing the porous osteoconductive component on the surface of an implant. The porous structure can be of metal. For example, the Cassidy patent application states, at ¶¶48-49: "These materials [i.e. of the porous structure] can include bioactive ceramic materials (e.g., hydroxyapatite, tricalcium phosphate, and fluoroapatite), ceramics (e.g., alumina and zirconia), metals and combinations of these materials. . . . Metals that can be used to form the porous element include titanium, stainless steels, cobalt/chromium alloys, tantalum, titanium-nickel alloys such as Nitinol and other superelastic metal alloys." The Johnson references state: "Metals which can be used to form the hard, strong, continuous framework component include titanium, stainless steels, cobalt/chrome alloys, tantalum, titanium-nickel alloys such as Nitinol and other superelastic metal alloys." Each of these patent documents mentions calcium sulfate, but only in passing. The Johnson patents make only one reference to calcium sulfate, as follows: "Examples of ceramic materials for the osteoconductive portion include calcium phosphates (e.g., hydroxyapatite, fluorapatite, and tricalcium phosphate and mixtures thereof), bioactive glasses, osteoconductive cements, and compositions containing calcium sulfate or calcium carbonate." The Cassidy application makes only one reference to calcium sulfate, as follows: "For medical applications, osteoconductive and osteoinductive materials can be included with both the porous and dense elements. The osteoconductive and osteoinductive materials that are appropriate for use in the present invention are biologically acceptable and include such osteoconductive materials as collagen and the various forms of calcium phosphates including hydroxyapatite; tricalcium phosphate; and fluoroapatite, bioactive glasses, osteoconductive cements, and compositions containing calcium sulfate or calcium carbonate . . ." Thus, the Johnson and Cassidy references do not specifically teach the use of bulk form calcium sulfate hemihydrate, applying the calcium sulfate in the form of an aqueous solution, nor wiping to remove excess calcium sulfate.

As far as the applicant can determine, the only instance in which a wiping operation has been applied to a coating on an implantable device appears in U.S. PAP 2001/0014717 A1 (Hossainy) and its family members. U.S. PAP 2001/0014717 A1 states, at ¶0083: "Application of the composition can be by any conventional method, such as by spraying the composition onto the prosthesis or immersing the prosthesis in the composition. Operations such as wiping, centrifugation, blowing, or other web clearing acts can also be performed to achieve a more uniform coating. Briefly, wiping refers to physical removal of excess coating from the surface of the stent; . . ." The Houssainy application is directed toward stents. The application does not discuss porosity or pores, and likewise provides no teaching concerning using a wiping process to preserve a load bearing surface of a porous layer. The Houssainy application mentions calcium sulfate only once, in ¶0073, as being one of dozens of "particles" suitable for use in a composition for forming a rate reducing membrane. Houssainy states that "particles of inorganic or organic type are added to the blend. The particles should be dispersed in the blend. Dispersed is defined as the particles being present as individual particles, not agglomerates or flocs." (¶ 0071) Houssainy's definition of "dispersed" thus excludes use of calcium sulfate in the crystalline calcium sulfate hemihydrate form contemplated by the present invention.

As mentioned above, applicant Wright Medical Technology, Inc. is a leading manufacturer of calcium sulfate-based bone repair materials. Applicant has discovered that at least one of its products, OSTEOSET® resorbable bead kit, can be used in the efficient process describe below to provide an implant that has both a porous load bearing surface and an impregnated bioresorbable calcium sulfate layer. There is thus a need for a method of preparing or manufacturing a coated implant having the following characteristics and advantages over the prior art.

OBJECTS AND SUMMARY OF THE INVENTION

It is an object of the invention to provide an implant that promotes increased bone in-growth.

It is another object of the invention to provide a practical intra-operative method of preparing an orthopedic implant for promotion of bone in-growth.

It is another object of the invention to provide an efficient and economical method of manufacturing an orthopedic implant for promotion of bone in-growth.

A method of preparing an implant for bone in-growth comprising: providing a metal implant body, the metal implant body having a metal load bearing layer formed on at least a portion of an outer surface of the implant body, the metal load bearing layer having a plurality of pores therein, the pores configured to promote bone in-growth into the load bearing layer; providing calcium sulfate hemi-hydrate; providing a diluent; mixing the calcium sulfate hemi-hydrate and the diluent to form a calcium sulfate paste; applying the calcium sulfate paste to the load bearing layer such that the calcium paste substantially impregnates at least a portion of the pores and forms an excess layer of the calcium sulfate paste on an outer surface of the load bearing layer; and wiping the calcium sulfate paste to remove the excess layer and thereby expose the outer surface of the load bearing layer while leaving the calcium sulfate paste impregnated in the pores. The calcium sulfate paste undergoes a phase change into a hardened calcium sulfate dihydrate coating impregnated in the pores. During the phase change to calcium sulfate dihydrate, the calcium sulfate paste expands in volume, which assists in holding the calcium sulfate dihyrdrate coating within the pores. The calcium sulfate paste is preferably between about 23 to about 100 parts by weight diluent to about 100 parts by weight calcium sulfate hemihydrate. In a preferred embodiment, the calcium sulfate paste is about 70 parts by weight diluent to about 100 parts by weight calcium sulfate hemihydrate. Implants can be formed using the methods disclosed herein. A kit can be provided to facilitate use of the method disclosed herein.

The foregoing and other objects, features, aspects and advantages of the invention will become more apparent from the following detailed description of the invention when considered in conjunction with the accompanying drawings.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

As shown in FIGS. 1-4, the invention consists generally of a method of preparing an implant 10 for enhanced bone in-growth by applying and then wiping off a calcium sulfate paste 50. FIGS. 1-4 show a representative view of a cross-section of a portion of an implant body 10. The implant body 10 is made of metal. A load bearing layer 20 is formed on at least a portion of an outer surface 12 of the implant body 10. The load bearing layer 20 has a plurality of pores 30 therein. The pores 30 are configured to promote bone in-growth into the load bearing layer 20. In the representative view of FIGS. 1-4, the load bearing layer 20 is a plurality of beads, but the load bearing layer 20 can be formed of any porous material suitable for providing a load bearing surface on an implant, such as plasma spray (FIG. 7), fiber metal (FIG. 8), or the various metal porous layers discussed in the background section of this specification.

Figure 1:
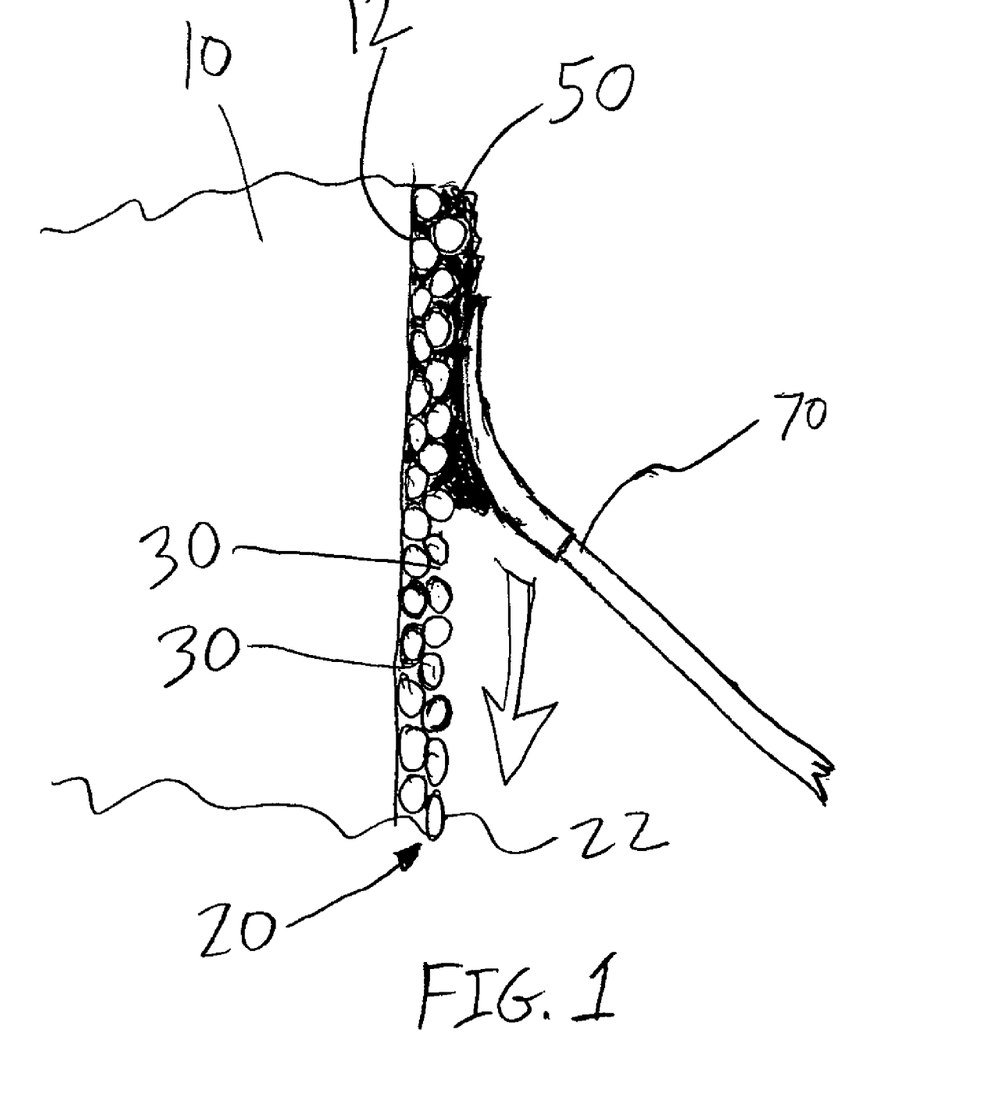
FIG. 1 is a side cross-section view of a representative implant surface, showing one preferred method of applying calcium sulfate solution to a porous load bearing layer of the implant.
Figure 2:
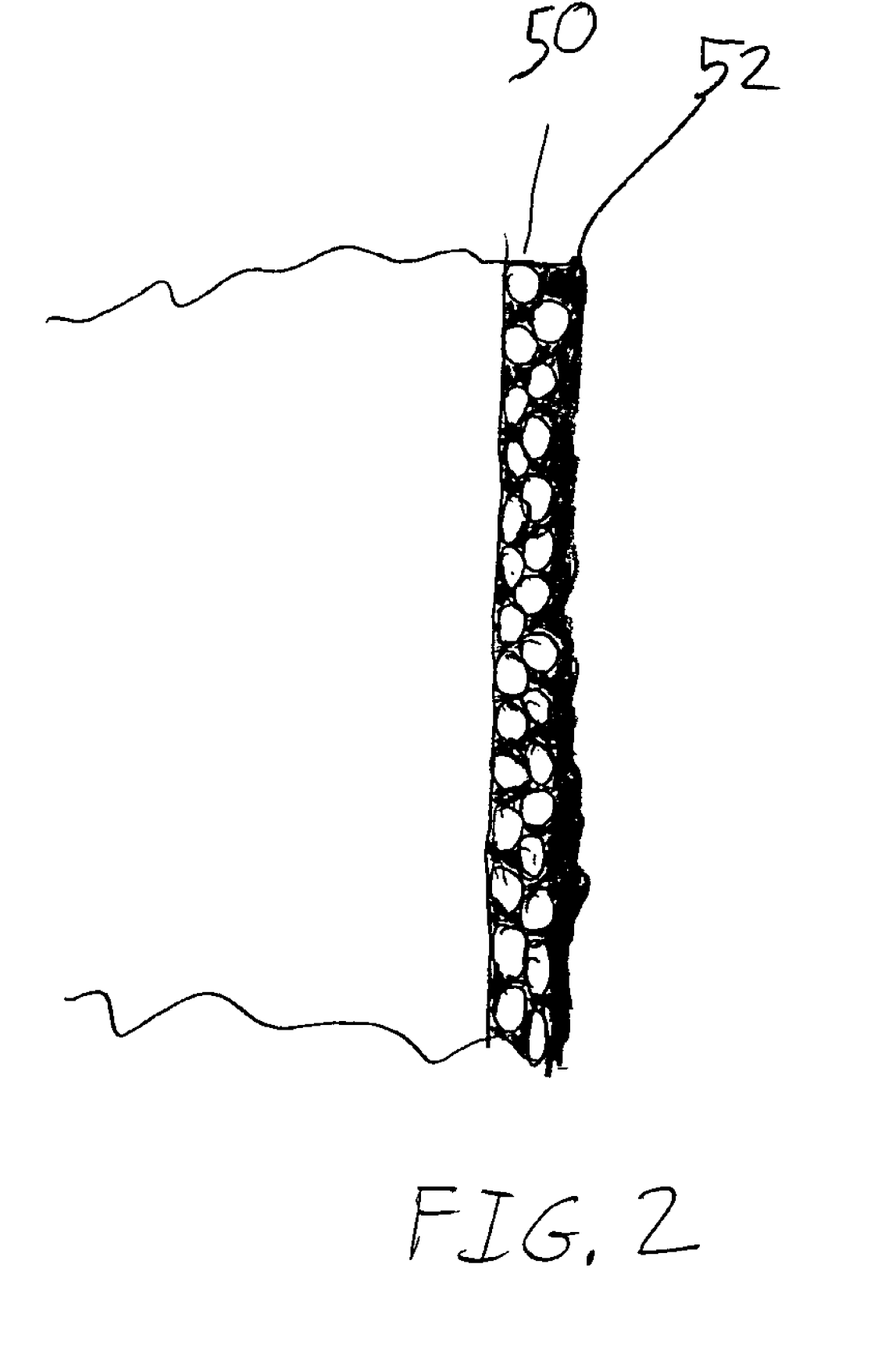
FIG. 2 is a side cross-section of the representative implant surface of FIG. 1 after a porous load bearing layer has been impregnated and covered with a calcium sulfate solution.
Figure 3:
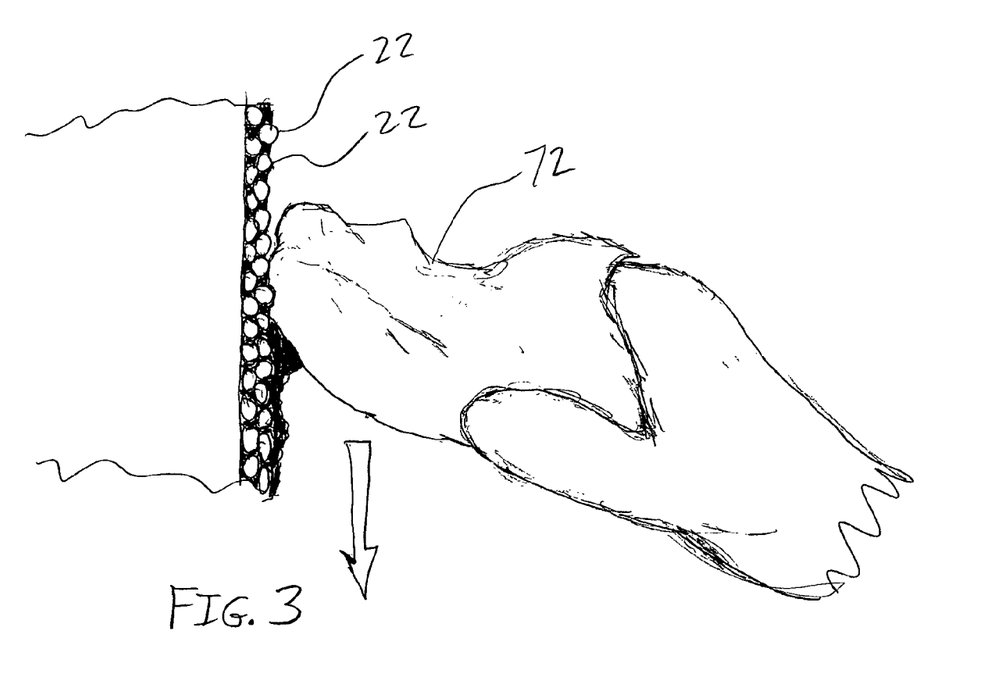
FIG. 3 is a side cross-section view of the representative implant of FIGS. 1-2 showing one preferred method of wiping excess calcium sulfate to allow a load bearing surface of the porous coating to stand proud above the calcium sulfate solution.
Figure 4:
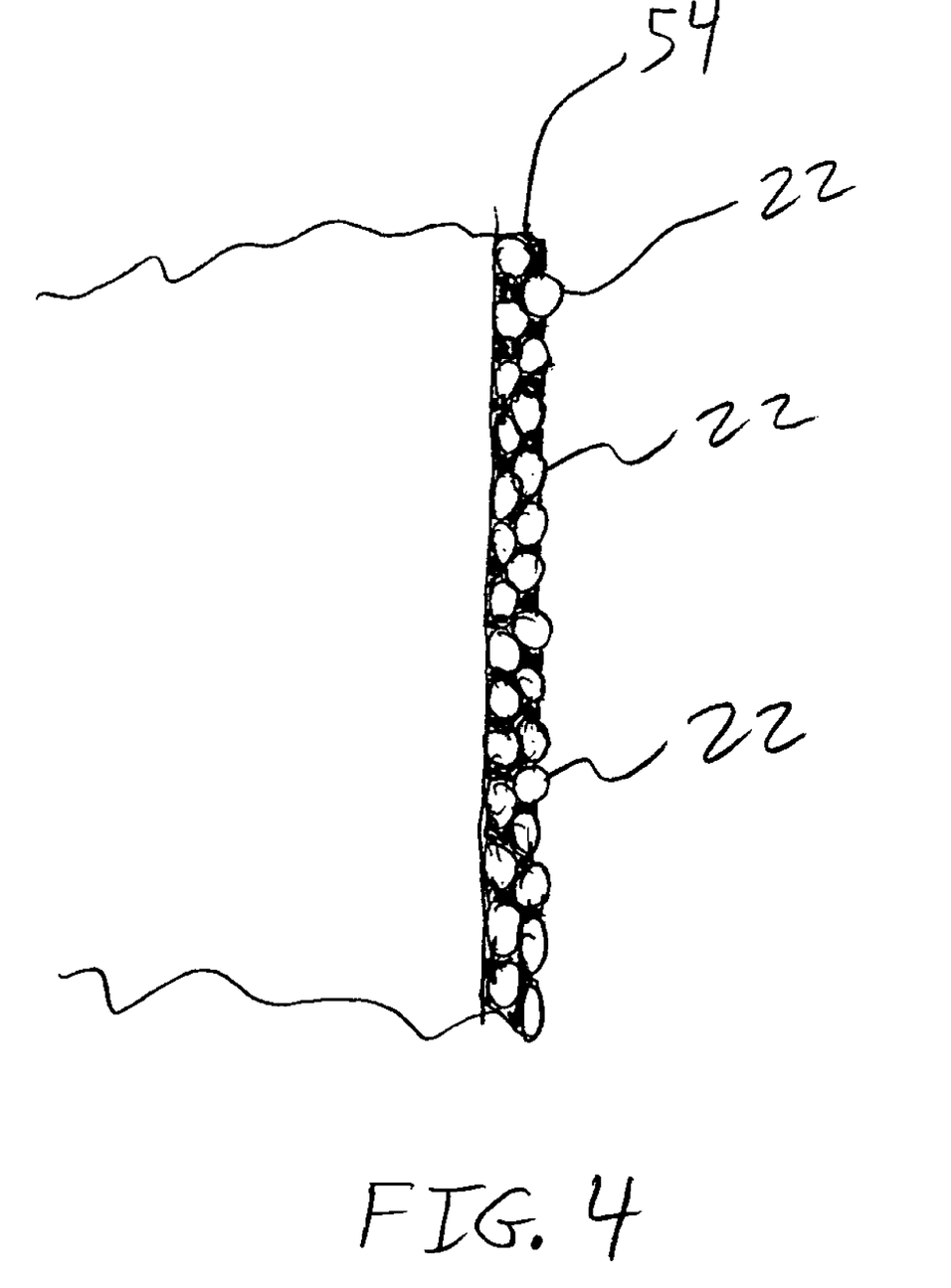
FIG. 4 is a side cross-section view of the representative implant surface of FIGS. 1-3 after completion of the wiping procedure.
Figure 5:
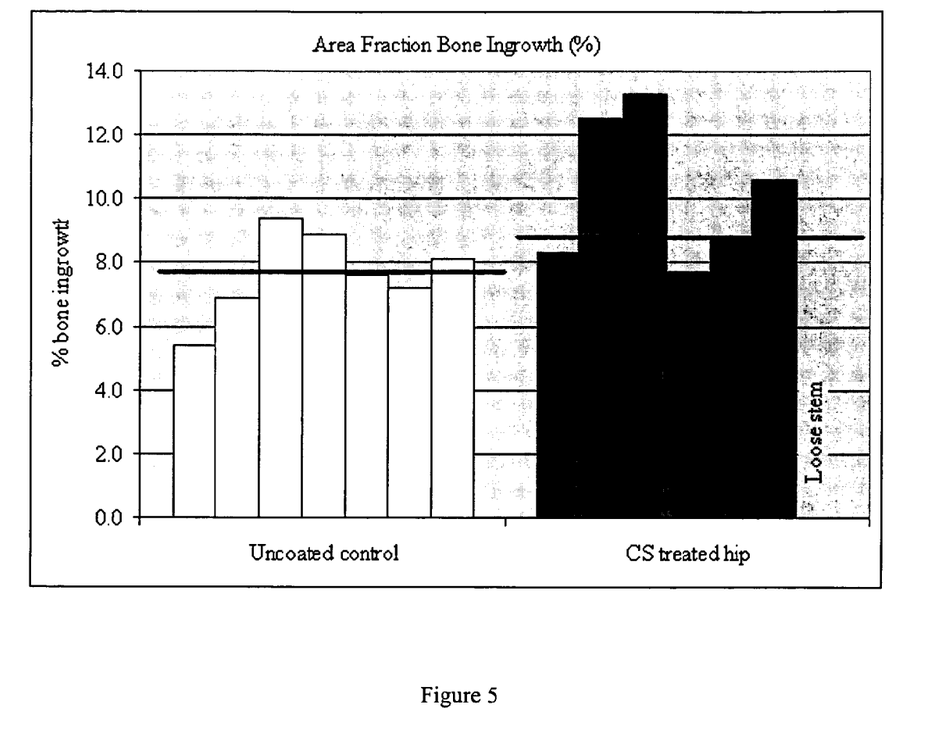
FIG. 5 is a graph showing improved bone in-growth provided by the invention.
Figure 6A:
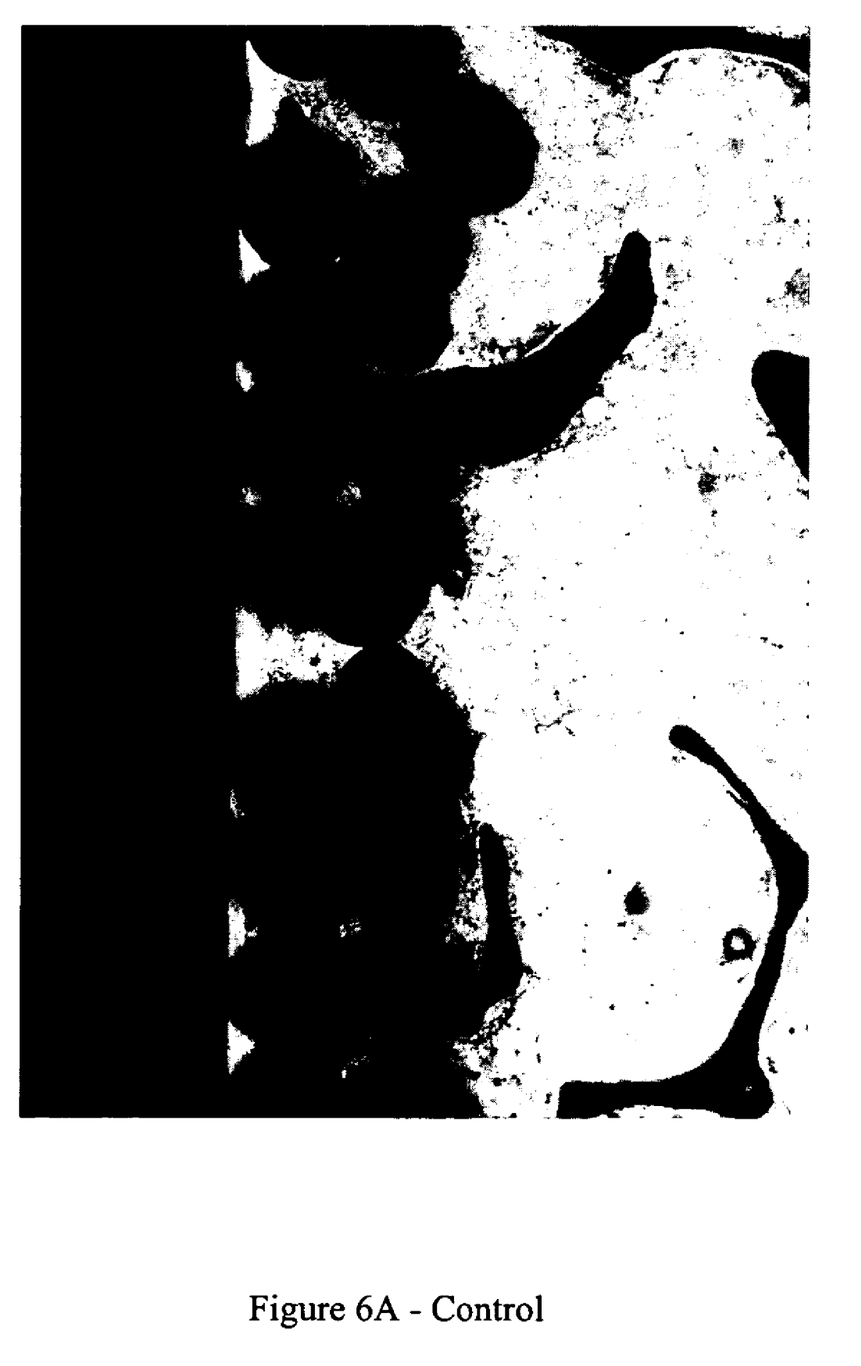
FIG. 6A is a photograph showing bone in-growth in a control implant that was not treated with calcium sulfate.
Figure 6B:
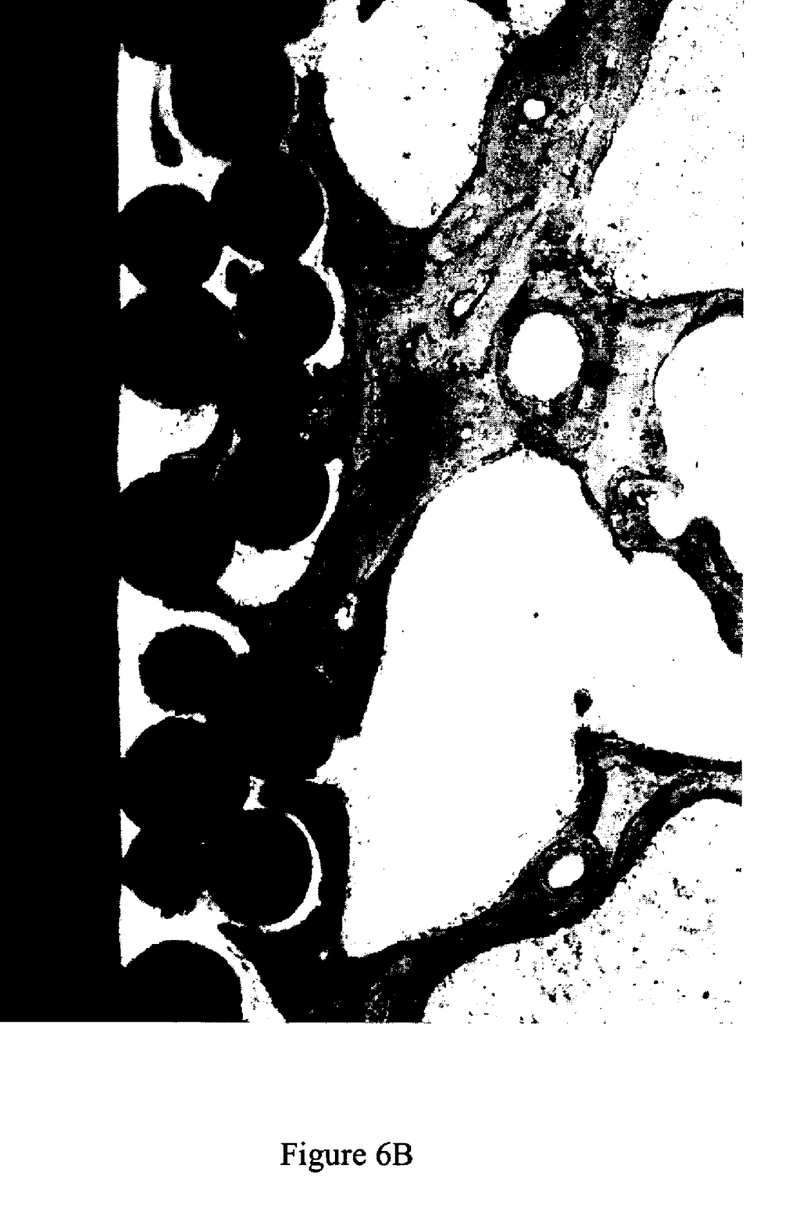
FIG. 6B is a photograph showing increased bone in-growth in an implant that was treated with calcium sulfate using the method of the invention.

As indicated in FIG. 1, a calcium sulfate paste 50 is applied to an outer surface 12 of the implant body 10. The calcium sulfate paste 50 is preferably formed from calcium sulfate hemihydrate powder and a diluent such as sterile water or saline. The calcium sulfate paste 50 may include further ingredients, such as demineralized bone matrix, accelerants designed to accelerate the reaction of calcium sulfate hemihydrate to calcium sulfate dihydrate, plasticizers, medicaments, or biologically active agents such as growth factors. As indicated in FIG. 1, the calcium sulfate paste 50 is applied to the load bearing layer 20 such that the calcium paste 50 substantially impregnates at least a portion of the pores 30. FIG. 1 shows a preferred method in which a spatula 70 serves as a means for applying the paste, but other techniques such as dipping/immersion, injection, spraying or other methods of wiping can be used, provided that the calcium sulfate paste 50 provides a desired level of impregnation of the pores 30. As shown in FIG. 2, the calcium sulfate paste 50 forms an excess layer 52 of calcium sulfate paste 50 on an outer surface 22 of the load bearing layer 20. As shown in FIG. 3, wiping is used to remove the excess layer 52 of calcium paste 50 and thereby expose the outer surface 22 of the load bearing layer 20 while leaving the calcium sulfate paste 50 impregnated in the pores 30. Exposure of the outer surface 22 of the load bearing layer 20 ensures that intimate contact and load transmission between the bone and the implant occurs through the exposed (uncoated) area. Although FIG. 3 shows an preferred embodiment in which a cloth 72 is used as the wiping means, other means such as brushes or sponges could be used. As shown in FIG. 4, after wiping, the peaks of the load bearing layer 20 stand proud and are able to serve a load bearing function without interference from an overlying layer of calcium sulfate. The load bearing layer also protects the impregnated calcium sulfate 50 from deterioration, such as from cracking or delamination.

Once the excess layer 52 of calcium sulfate hemihydrate paste 50 has been removed, the remaining calcium sulfate hemihydrate paste 50 crystallizes to leave a hardened calcium sulfate dihydrate coating 54 impregnated in the pores 30. During this phase conversion, the calcium sulfate material undergoes a volume expansion, which further serves to hold the material within the pores 30. Crystallization can take place before or after implantation.

The calcium sulfate paste 50 preferably is between about 23 to about 100 parts by weight diluent to about 100 parts by weight calcium sulfate hemihydrate. The calcium sulfate paste 50 more preferably is between about 30 to about 80 parts by weight diluent to about 100 parts by weight calcium sulfate hemihydrate. In a preferred embodiment, the calcium sulfate paste is about 70 parts by weight diluent to about 100 parts by weight calcium sulfate hemihydrate.

Figure 7:
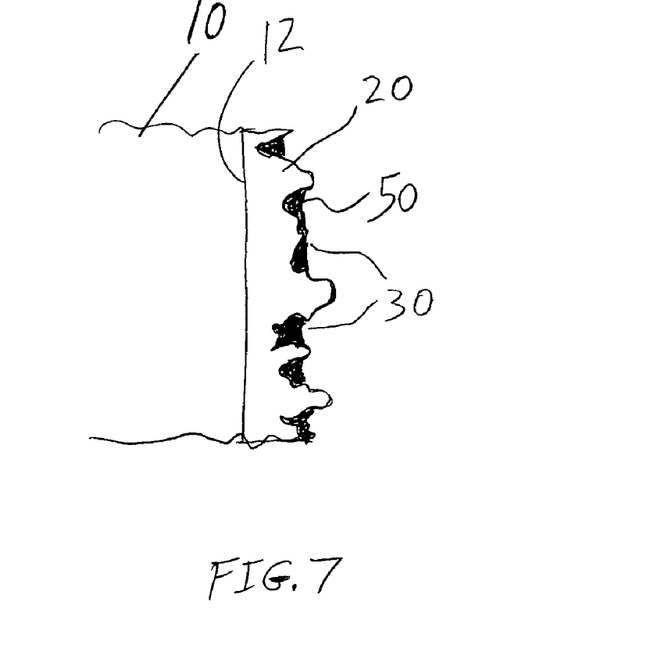
FIG. 7 is a side cross-section view of a representative implant surface having a plasma coating impregnated with calcium sulfate.
Figure 8:
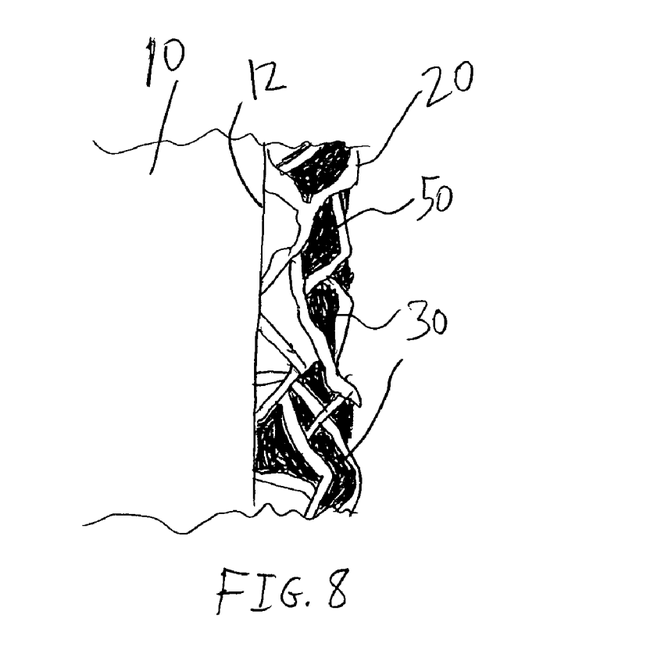
FIG. 8 is a side cross-section view of a representative implant surface having a fibrous metal structure impregnated with calcium sulfate.

As used herein, "pore" means a space or opening within a surface or body of a solid object. In the implant embodiment 10 of FIGS. 1-4, the load bearing layer 20 and the pores 30 have a 3-3 interconnected structure. However, the pores 30 need not be interconnected to attain the objectives of the invention. The concept of connectivity is explained at greater length in Newnham et al. "Connectivity and Piezoelectric-Pyroelectric Composites," Materials Research Bulletin, Vol. 13 pp. 525-536 (1978), the teachings of which are incorporated herein by reference. A material with all isolated (that is, dead end) pores in a dense matrix would have 3-0 connectivity. A material having pores that pass completely through the matrix in one dimension would yield 3-1 connectivity, and a material having pores that interconnect two perpendicular faces but not the third would have 3-2 connectivity. FIG. 7 provides a side cross-section view of a representative implant surface having a porous plasma coating impregnated with calcium sulfate. FIG. 8 provides a side cross-section view of a representative implant surface having a porous fibrous metal structure impregnated with calcium sulfate.

Methods of making a calcium sulfate hemihydrate are described in U.S. Pat. Nos. 5,614,206, 5,807,567, and 6,030,636, all of which are incorporated herein by reference. Preferred calcium sulfate powder includes CAPSET™ powder (available from LifeCore of Chaska, Minn.) which is composed of alpha-calcium sulfate hemihydrate; HAPSET™ powder (also available from LifeCore) which is composed of alpha-calcium sulfate hemihydrate blended with granular hydrated calcium sulfate; and OSTEOSET® powder (available from Wright Medical Technology, Inc. of Arlington, Tenn.) which is composed of alpha-calcium sulfate hemihydrate.

If additives are desired, they may be mixed with the calcium sulfate in powdered form prior to mixing with a solution comprising water or dissolved in the solution and subsequently impregnated into the calcium sulfate powder. The additive preferably comprises from 0 to about 25 wt. % of the calcium sulfate powder, more preferably about 2 wt. % to about 10 wt. %, and most preferably about 2 wt. % to about 5 wt. %. Examples of additives which may be mixed in the calcium sulfate matrix are medicaments or pesticides. Examples of medicaments which may be mixed with the calcium sulfate matrix are antibiotics, chemotherapeutic agents, growth factors, and analgesics. Examples of antibiotics are tetracycline hydrochloride, vancomycin, cephalosporins, and aminoglycocides such as tobramycin and gentamicin. Examples of chemotherapeutic agents are cis-platinum, ifosfamide, methotrexate, and doxorubicin hydrochloride (ADRIAMYCIN® chemotherapeutic agent). Examples of growth factors are transforming growth factor beta (TGF-Beta), bone morphogenic protein (BMP), basic fiberblast growth factor, platelet-derived growth factor, and other polypeptide growth factors. Examples of analgesics are anesthetics such as lidocaine hydrochloride (XYLOCAINE® analgesic), bipivacaine hydrochloride (MARCAINE® analgesic), and non-steroidal anti-inflammatory drugs such as ketorolac tromethamine (TROADOL® anti-inflammatory).

The implant 10 can be prepared intra-operatively, such as immediately before implantation. Mixing about 25 grams of sterile calcium sulfate hemihydrate powder with about 17.5 cc of sterile water (i.e. about 70 parts calcium sulfate to about 100 parts water) provides an ideal consistency and batch size for carrying out the method of the invention in an operating room. In the operating room, the calcium sulfate paste 50 is preferably formed using an OSTEOSET® Resorbable Bead Kit, which is available from Wright Medical Technology, Inc., Arlington, Tenn. One advantage of preparing the implant intra-operatively is that the surgeon can selectively incorporate adjuncts to the calcium sulfate paste, such as antibiotics or analgesics. To facilitate use of the method in an intra-operative setting, a kit can be provided containing the requisite materials for conveniently preparing an implant for bone in-growth. For example, the kit could include calcium sulfate hemihydrate powder, a diluent, a mixing bowl, a spatula, and a wiping cloth. The kit could also include an implant to be coated with calcium sulfate.

Alternatively, the implant 10 can be provided with the calcium sulfate coating 54 preformed in the pores 30. The later technique has the advantage of allowing for efficiency and economy in the manufacturing process, since implants can be prepared in batches in manufacturing facilities, and then distributed for use, such as in the form of a surgical kit. Manufacturing also allows for various and increased quality control measures, such as ensuring that residual layers of calcium sulfate do not form part of the load bearing surface.

The coating process of the invention can be used with any type of implant in which bone in-growth is beneficial for securing the implant, such as acetabular shells and femoral stems.

Experimental

Introduction: As mentioned above, maximizing bone ingrowth in the early reparative phase following insertion of an implant is believed to be important to long-term fixation of cementless components for joint replacement. It was hypothesized that the application of $CaSO_4$ paste to the porous surface might increase the amount of bone ingrowth into the pores. Using a 26-week canine primary Total Hip Replacement ("THR") model, the amount of bone ingrowth, the nature of the interface tissues, serum calcium levels, and tibial bone mineral content (BMC) were compared between groups receiving porous coated femoral stems with and without the application of $CaSO_4$ paste.

Materials and Methods: Under an animal care committee-approved protocol, 14 adult canines (28-41 kgs) had unilateral THR using a Ti-6Al-4V femoral stem fully coated with beads. A conventional PE acetabular cup was fixed with bone cement. The femoral canal was prepared using a broach under-sized to the stem by 0.8 mm. Just prior to insertion of the stems in 7 dogs, a calcium sulfate paste, made by mixing calcium sulfate hemihydrate powder with water, was applied over the bead surface and into the pores using a spatula. The paste was made by mixing 25 grams of sterile calcium sulfate hemihydrate powder with 17.5 cc of sterile water, using the ingredients of an OSTEOSET® Resorbable Bead Kit (available from Wright Medical Technology, Inc., Arlington, Tenn.). Excess paste was wiped from the implants leaving the outer beads proud. The applied paste was allowed to air dry in the pores for 1 minute before the component was impacted into the prepared femoral canal. The other 7 dogs received identical stems without the paste as the control. One dog was excluded from the study because of intraoperative instability of the stem due to poor bone quality, leaving 6 test and 7 control animals for analysis.

Serum calcium levels were determined in the CaSO4 paste-treated group from blood samples collected pre-op, at 1, 24 and 72 hrs, and at 1, 4, 12, and 26 wks. Radiographs were obtained pre and postoperative and at 4, 12 and 26 wks. After 26 wks, the femur/implant construct was sectioned transversely and the nature of the ingrown and periprosthetic tissues was studied from stained sections using light microscopy. The area fraction of bone ingrowth was determined from BSE SEM images at 5 levels of the stem. Postmortem BMC of the right and left tibiae was determined using DEXA. The data were analyzed using the Mann-Whitney and Friedman tests.

Results: Clinically, all animals were weight bearing within 2 wks, exhibited normal ambulation within 4 wks, and maintained normal function throughout the study.

The mean area fraction of bone ingrowth was significantly greater in stems treated with $CaSO_4$ paste (10.2±2.3%) compared to the untreated control stems (7.6%±1.3%) (p=0.046). Notably, at every level of the stem, the area fraction of bone was greater in the treated compared to the control implants. No residual $CaSO_4$ was detected by backscattered electron imaging either within the pores or in the adjacent medullary bone.

In the stained sections, residual solid or particulate $CaSO_4$ paste was not present within the porous coating, adjacent tissues, or the joint capsule. There were no remarkable differences between the treated and control specimens with regard to the nature of the ingrown or interface tissues. Within the pores and at the implant-host bone interface, the tissues consisted primarily of matured bone trabeculae and marrow. There was often a fibrous membrane present at the junction of the beads and the substrate of the stem in both groups.

Mean serum calcium peaked at 1 wk (10.9±0.2 mg/dl) and was significantly higher than the mean preoperative value (10.5±0.3 mg/dl) (p=.046). There were no other significant differences between the mean preoperative and postoperative time points. For all samples, mean serum calcium ranged from 10.1 to 10.9 mg/dl and were well within the normal range for canines (7.9 to 11.5 mg/dl).

DEXA of the paired tibiae revealed overall slightly lower values of BMC in the bones of the operated limb compared to those from the opposite limb in both the treated and control groups, as expected. The mean reduction in tibial BMC was 5.9±2.4% for the treated and 4.2±1.8% for the control implant group (p=.199), suggesting that the operated limbs in the two groups had been used to a similar degree.

The clinical and specimen radiographs revealed implant-bone interfaces consistent with bone ingrowth into the porous coating for both the $CaSO_4$-treated and control implants. None of the implants migrated from their initial positions. There were no radiolucencies at the implant-host bone interface and no evidence of osteolysis. No qualitative differences in medullary bone density or cortical remodeling were noted between the two groups.

Discussion: The application of $CaSO_4$ paste to the porous surface of a hip replacement femoral stem resulted in a 34% increase in bone ingrowth. The increased bone ingrowth was maintained in a weight-bearing implant up to 6 months, well past completion of the healing and early remodeling phases. Previous studies have demonstrated the efficacy of $CaSO_4$ as pellets, putty, or paste for restoration of bone defects. In the setting of cementless, porous coated implants, the relatively rapid resorption of $CaSO_4$ and its replacement with new bone are essential attributes to avoid impeding bone ingrowth by pore occlusion. The application of $CaSO_4$ paste has important potential for enhancing bone ingrowth into implants for primary reconstructions and holds promise in the bone-deficient environment of revision hip replacement as well.

Conclusion: Application of $CaSO_4$ paste to a porous surface significantly increased bone ingrowth in a canine model of primary total hip replacement.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A method of preparing an implant for bone in-growth comprising:
providing a metal implant body, said metal implant body having a metal load bearing layer formed on at least a portion of an outer surface of the implant body, said metal load bearing layer having a plurality of pores therein, said pores configured to promote bone in-growth into said load bearing layer,
providing calcium sulfate hemi-hydrate,
providing a diluent,
mixing said calcium sulfate hemi-hydrate and said diluent to form a calcium sulfate paste,
applying said calcium sulfate paste to said load bearing layer such that said calcium paste substantially impregnates at least a portion of said pores and forms an excess layer of said calcium sulfate paste on an outer surface of said load bearing layer, and
wiping said calcium sulfate paste to remove said excess layer and thereby expose said outer surface of said load bearing layer while leaving said calcium sulfate paste impregnated in said pores.

2. The method of claim 1, wherein said calcium sulfate paste undergoes a phase change into a hardened calcium sulfate dihydrate coating impregnated in said pores, said calcium sulfate paste expanding in volume during said phase change to said calcium sulfate dihydrate coating to thereby assist in holding said calcium sulfate dihyrdrate coating within said pores.

3. The method of claim 1, wherein said calcium sulfate paste is between about 23 to about 100 parts by weight diluent to about 100 parts by weight calcium sulfate hemihydrate.

4. The method of claim 1, wherein said calcium sulfate paste is about 70 parts by weight diluent to about 100 parts by weight calcium sulfate hemihydrate.

5. The method of claim 1, wherein said pores are interconnected.

6. The method of claim 1, wherein said metal load bearing layer is selected from the group consisting of beads, plasma spray, and fibers.

7. An orthopedic implant comprising:
a metal implant body, said metal implant body having a load bearing layer fixed on at least a portion of an outer surface of the implant body, said load bearing layer having a plurality of pores therein, said pores configured to promote bone in-growth into said load bearing layer,
said pores of said load bearing layer impregnated with a calcium sulfate coating below an outer surface of said load bearing layer,
said calcium sulfate coating formed by applying a calcium sulfate paste to said load bearing layer such that said calcium paste substantially impregnates at least a portion of said pores and forms an excess layer of said calcium sulfate paste on an outer surface of said load bearing layer, and wiping said calcium sulfate paste to remove said excess layer and thereby expose said outer surface of said load bearing layer while leaving said calcium sulfate paste impregnated in said pores.

8. The implant of claim 7, wherein said calcium sulfate paste undergoes a phase change into a hardened calcium sulfate dihydrate coating impregnated in said pores, said calcium sulfate paste expanding in volume during said phase change to said calcium sulfate dihydrate coating to thereby assist in holding said calcium sulfate dihydrate coating within said pores.

9. The implant of claim 7, wherein said calcium sulfate paste is between about 23 to about 100 parts by weight of a diluent to about 100 parts by weight of a calcium sulfate hemihydrate.

10. The implant of claim 7, wherein said calcium sulfate paste is about 70 parts by weight of a diluent to about 100 parts by weight of a calcium sulfate hemihydrate.

11. The implant of claim 7, wherein said pores are interconnected.

12. The implant of claim 7, wherein said metal load bearing layer is selected from the group consisting of beads, plasma spray, and fibers.

13. A kit for intra-operative preparation of a porous load bearing surface of an orthopedic implant for bone in-growth comprising:
an orthopedic implant including a porous load bearing surface,
calcium sulfate hemi-hydrate,
a diluent,
a sterile mixing vial for holding said calcium sulfate hemihydrate and said diluent during mixing,
a mixer for mixing said calcium sulfate hemi-hydrate and said diluent in said vial to form a calcium sulfate paste,
a spreader for applying said calcium sulfate paste to the porous load bearing surface of the implant, and
a means for wiping an excess portion of said calcium sulfate paste from the porous load bearing surface of the implant to thereby expose an outer surface of the load bearing surface.

14. The kit of claim 13, wherein said orthopedic implant includes a metal implant body.

15. The kit of claim 13, wherein between about 23 to about 100 parts by weight diluent are provided to about 100 parts by weight calcium sulfate hemihydrate.

16. The kit of claim 13, wherein about 70 parts by weight diluent is provided to about 100 parts by weight calcium sulfate hemihydrate.

17. The kit of claim 13, further comprising an antibiotic for incorporation into said calcium sulfate paste.

18. The kit of claim 13, wherein said means for wiping is a cloth.

19. The kit of claim 14, wherein the implant is a femoral hip stem.

20. The kit of claim 14, wherein the implant is an acetabular shell.

* * * * *